(12) United States Patent
Fitzgerald et al.

(10) Patent No.: US 10,149,964 B2
(45) Date of Patent: Dec. 11, 2018

(54) STRETCHABLE SLEEVE AND WRAP FOR PROTECTING AND SECURING CATHETER DRESSINGS AND TUBES ON A PATIENT

(76) Inventors: Michael Fitzgerald, Danvers, MA (US); Kezia Fitzgerald, Danvers, MA (US)

( * ) Notice: Subject to any disclaimer, the term of this patent is extended or adjusted under 35 U.S.C. 154(b) by 0 days.

(21) Appl. No.: 13/545,937

(22) Filed: Jul. 10, 2012

(65) Prior Publication Data
US 2013/0012883 A1  Jan. 10, 2013

Related U.S. Application Data

(60) Provisional application No. 61/506,148, filed on Jul. 10, 2011.

(51) Int. Cl.
| | | |
|---|---|---|
| *A61M 25/02* | (2006.01) | |
| *A61M 5/14* | (2006.01) | |
| *A61M 39/08* | (2006.01) | |
| *A61F 13/14* | (2006.01) | |

(Continued)

(52) U.S. Cl.
CPC .............. *A61M 25/02* (2013.01); *A61F 13/10* (2013.01); *A61F 13/143* (2013.01); *A61M 5/1418* (2013.01); *A61M 39/08* (2013.01); *A61M 2005/1586* (2013.01); *A61M 2025/0206* (2013.01); *A61M 2025/0213* (2013.01)

(58) Field of Classification Search
CPC .......... A61M 25/02; A61M 2005/1586; A61M 2025/0206; A61M 2025/0213; A61M 25/0206; A61M 5/32; A61M 5/1418; A61M 2025/0216; A61M 39/08; A61M 25/06; A61M 5/06; A61F 13/10; A61F 13/143

USPC .................. 604/93.01, 174–180, 891.1, 198
See application file for complete search history.

(56) References Cited

U.S. PATENT DOCUMENTS

| | | |
|---|---|---|
| 3,657,741 A | 4/1972 | Blano |
| 3,970,316 A | 7/1976 | Westmoreland, Jr. |
| D263,745 S | 4/1982 | Sandel |

(Continued)

FOREIGN PATENT DOCUMENTS

| | | |
|---|---|---|
| EP | 0424275 A1 | 4/1991 |
| WO | WO 2008/088556 A1 | 7/2008 |
| WO | WO 2013/009783 A1 | 1/2013 |

OTHER PUBLICATIONS

International Search Report and Written Opinion of the International Search Authority ISA for International Application No. PCT/US2012/046121, dated Sep. 28, 2012.

(Continued)

*Primary Examiner* — Imani Hayman
*Assistant Examiner* — Tiffany Legette-Thompson
(74) *Attorney, Agent, or Firm* — Daniel N. Smith

(57) ABSTRACT

An easily removable, non-irritating stretchable sleeve or chest wrap for protecting and securing a PICC line or chest catheter tubing and cap extending externally from the insertion point. The sleeve or chest wrap is easily attached to a patient's arm or body, securing the small length of the external PICC line or the central venous catheter, protecting the tubing and cap from external contaminants, and allowing easy access to the PICC line or the central venous catheter for administration of drugs or nutrients, and access for blood draws. This sleeve allows the patient freedom of movement and is comfortable enough to prevent skin irritation over long-term usage.

13 Claims, 11 Drawing Sheets

(51) Int. Cl.
*A61F 13/10* (2006.01)
*A61M 5/158* (2006.01)

(56) References Cited

U.S. PATENT DOCUMENTS

| | | | |
|---|---|---|---|
| 4,470,410 A | 9/1984 | Elliott | |
| 4,590,939 A | 5/1986 | Sakowski | |
| 4,591,356 A | 5/1986 | Christie | |
| 4,610,245 A | 9/1986 | Biearman | |
| 4,666,432 A * | 5/1987 | McNeish | A61M 25/02 128/DIG. 26 |
| 4,671,787 A | 6/1987 | Willman | |
| 4,870,976 A | 10/1989 | Denny | |
| D316,915 S | 5/1991 | Dryzal | |
| 5,188,608 A | 2/1993 | Fritts | |
| 5,407,422 A | 4/1995 | Matthijs et al. | |
| 5,468,229 A * | 11/1995 | Chandler | A61M 25/02 128/DIG. 26 |
| 5,496,282 A | 3/1996 | Millizer et al. | |
| 5,507,794 A | 4/1996 | Allen | |
| 5,720,713 A | 2/1998 | Hutchison | |
| 5,817,038 A | 10/1998 | Orange et al. | |
| 5,832,928 A | 11/1998 | Padilla, Jr. | |
| 5,897,519 A * | 4/1999 | Shesol | A61M 25/02 602/75 |
| 5,924,130 A | 7/1999 | Fragomeli | |
| 6,032,289 A | 3/2000 | Villapiano | |
| 6,042,568 A | 3/2000 | Gomez | |
| D435,911 S | 1/2001 | Yeager | |
| D444,240 S | 6/2001 | Bautista, Jr. | |
| 6,258,066 B1 | 7/2001 | Urich | |
| 6,267,115 B1 | 7/2001 | Marshel | |
| D456,521 S | 4/2002 | Griffin et al. | |
| 6,464,669 B2 * | 10/2002 | Wilke | A61M 25/02 604/179 |
| 6,477,710 B1 * | 11/2002 | Ojoyeyi | A41D 13/1236 2/114 |
| D468,013 S | 12/2002 | Mason | |
| D475,140 S | 5/2003 | Anderson | |
| D487,171 S | 2/2004 | Miller | |
| 6,892,733 B2 * | 5/2005 | Clinton | A61F 5/0109 128/878 |
| D515,745 S | 2/2006 | Leyva | |
| D519,639 S | 4/2006 | Follman | |
| D548,892 S | 8/2007 | Wilson et al. | |
| D550,848 S | 9/2007 | Juta et al. | |
| D560,041 S | 1/2008 | Cook et al. | |
| 7,527,602 B2 | 5/2009 | Weaver et al. | |
| D595,858 S | 7/2009 | Kazel | |
| D595,859 S | 7/2009 | Young | |
| D627,074 S | 11/2010 | Ray | |
| D627,078 S | 11/2010 | Matsuo et al. | |
| D630,335 S | 1/2011 | Wise et al. | |
| D633,624 S | 3/2011 | Monopoli | |
| D634,900 S | 3/2011 | Eff | |
| 7,913,320 B2 | 3/2011 | Grissom | |
| D646,789 S | 10/2011 | Barth | |
| D650,085 S | 12/2011 | Rucker et al. | |
| D656,276 S | 3/2012 | Kurland | |
| D660,438 S | 5/2012 | Kennedy et al. | |
| 2003/0094179 A1 * | 5/2003 | Clinton | A61F 5/0109 128/875 |
| 2003/0158528 A1 * | 8/2003 | Irish | A61M 39/18 604/326 |
| 2007/0083163 A1 | 4/2007 | Rydell | |
| 2008/0071224 A1 * | 3/2008 | Forsyth | A61M 25/02 604/179 |
| 2008/0208130 A1 | 8/2008 | Furman | |
| 2009/0318874 A1 * | 12/2009 | Guthrie | 604/180 |
| 2010/0100019 A1 | 4/2010 | Chen et al. | |
| 2011/0089159 A1 | 4/2011 | Chen | |
| 2011/0125097 A1 * | 5/2011 | Shaw | A61M 5/158 604/164.12 |
| 2011/0301544 A1 | 12/2011 | Dixon | |

OTHER PUBLICATIONS

Partial Supplemental European Search Report of the European Patent Office for European Patent Application No. 12810538.4, dated May 29, 2015.

Extended European Search Report of the European Patent Office for European Patent Application No. 12810538.4, dated Sep. 25, 2015.

* cited by examiner

STRETCHABLE SLEEVE AND WRAP FOR PROTECTING AND SECURING CATHETER DRESSINGS AND TUBES ON A PATIENT

CROSS REFERENCE TO RELATED APPLICATION

This application claims the benefit of U.S. Provisional Patent Application No. 61/506,148 filed on Jul. 10, 2011, the contents of which are incorporated herein by reference.

FIELD OF THE INVENTION

This invention relates to easily removable, non-irritating stretchable sleeve or chest wrap for protecting and securing a PICC line or chest catheter tubing and cap extending externally from the insertion point.

BACKGROUND OF INVENTION

Intravenous or IV therapy involves administration of liquids directly into a patient's veins through an inserted catheter. Long-term, continuous IV therapy (for administrating chemotherapy regimens, frequent drawing of blood samples, antibiotic regimens, or tube feeding [parenteral nutrition]) is usually accomplished with a peripherally inserted central catheter line (or PICC line), or through a more central location with a central venous catheter or a Broviac catheter.

A PICC line is a soft, flexible tube, with one or more internal lumens. The PICC line is surgically inserted into a peripheral vein, often the arm, in a sterile procedure that must be undertaken by a trained medical professional. During insertion, the PICC line is drawn upward with an inserted guide wire until the tube is in, or proximate to, the superior vena cava of the heart. PICC lines are usually inserted 25 to 60 cm within a patient's peripheral vein.

A central venous catheter is a soft, flexible tube, with one or more internal lumens that has a larger diameter than a PICC line. A Broviac catheter is a central venous catheter with a smaller lumen for use with small children. The central venous catheter is placed directly into a large vein in the neck, chest, or groin.

PICC lines can remain in situ for extended periods of time, from days to a year. PICC lines and central venous catheters are more patient-friendly, because they necessitate only one tube insertion, rather than repeated ones.

Once the PICC line or the central venous catheter is inserted, the guide wire is removed and a small length of the PICC line or the central venous catheter remains external to the patient, extending outwards from the point of insertion. The external end of the PICC line or the central venous catheter is capped to prevent bacteria, viruses or contaminants from entering.

This small length of the PICC line or the central venous catheter often dangles, unsupported, near the point of insertion. There is a constant danger of pulling or otherwise interfering with the PICC line or the central venous catheter during normal daily activities or during sleep. Tape is generally used to secure the tubes while not in use. These tapes can lead to pain, inflammation, infections, and reduced drug efficacy. The problem in movement is especially pronounced in young children undergoing long-term therapy with a PICC line or a central venous catheter.

Thus, this small length of the PICC line or the central venous catheter, and the end cap, must be attached to the patient to prevent movement or dislodgment of the internal tubing. This movement or dislodgment may prevent the administered liquids from reaching the desired veins, or cause significant inflammation to the insertion point, air embolisms, arterial punctures, internal bruising, and blood clots.

The PICC line or the central venous catheter external attachment must also protect the tubing from being pierced or otherwise punctured due to movement. A pierced or punctured PICC line or central venous catheter, would not only prevent administered liquids from reaching the desired veins, it may also allow bacteria or contaminants to enter, causing internal infections in the patient.

Previous solutions to prevent movement of the PICC line or the central venous catheter have included taping the external small length of the lines with various medical tapes. These tapes often leave adhesive residues that are irritating to the skin. These irritations can often lead patients to inadvertently scratch the insertion points, thereby moving the small length of the external PICC line or the central venous catheter. Some newer medical tapes reduce or virtually eliminate adhesive residue, but these tapes are not as strong and still irritate the skin surrounding the insertion point. Furthermore, this medical tape must often be partially removed to access the PICC line or the central venous catheter and then re-taped once the IV therapy is complete. This removal of the tape and re-taping to the skin can result in significant irritation. Moreover, when the end of the PICC line or the central venous catheter is taped visibly from the outside of the patient's clothing, it presents an unsightly and disturbing appearance that can produce mental distress.

Accordingly, there is a need for a protective sleeve to protect the PICC line or the central venous catheter insertion points. This sleeve needs to be easily attached to a patient's arm or body, secure the small length of the external PICC line or the central venous catheter, protect the tubing and cap from external contaminants, and allow easy access to the PICC line or the central venous catheter for administration of drugs or nutrients, and access for blood draws. This sleeve must also allow the patient freedom of movement and be comfortable enough to prevent skin irritation over long-term usage.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a protective sleeve for an intravenous needle inserted into a vein in a patient's arm, wherein the short length of tube extends from the intravenous needle and comprises a cap on a distal end, the protective sleeve comprising: a stretchable tubular member having a first end with a first opening, a second end with a second opening, a substantially flat internal surface, a substantially flat external surface, a lumen substantially parallel with the longitudinal axis, wherein the patient's arm is slidably placed within the sleeve through the first opening through the lumen and then through the second opening such that a portion of the arm is contained within the sleeve and extends through both openings, further wherein the sleeve is positioned on the arm over the insertion point of the intravenous needle; the sleeve further comprising a slit opening between the internal and external surfaces that is positioned proximate to the intravenous needle insertion point, wherein the tube extending from the intravenous needle is placed through the slit opening; the sleeve comprising a substantially flat strap disposed on the external surface, distal from the slit opening, wherein the strap comprises a first end and a second end that are both attached to the external surface of the sleeve, further wherein a central portion of the strap is unattached to the external surface of the sleeve, further wherein the tube extending from the intravenous needle is placed through the strap; and the sleeve further comprising a substantially flat pocket disposed on external surface, distal from the strap, wherein the pocket comprises a pocket opening, further wherein the distal end of the tube extending from the intravenous needle is placed into the pocket through the pocket opening; wherein the slit opening, the strap and the pocket secure the tube extending from the intravenous needle to the sleeve and the patient's arm.

The subject invention also discloses a protective sleeve for a short length capped IV catheter tube extending from an insertion point in a patient's arm, the protective sleeve comprising: a stretchable cylindrical housing having a proximal end, a distal end, a substantially flat internal surface, a substantially flat external surface, an internal cavity passing through the proximal end to define a proximal opening, and further passing through the distal end to define a distal opening, wherein the patient's arm is slidably placed within the sleeve through the distal opening through the cavity and then through the proximal opening such that a portion of the arm is contained within the sleeve and extends through both openings, further wherein the sleeve is positioned on the arm over the insertion point; the sleeve further comprising a narrow opening between the internal and external surfaces that is positioned proximate to the insertion point, wherein the IV catheter tube is placed through the narrow opening; the sleeve comprising a substantially flat strap disposed on the external surface, distal from the narrow opening, wherein the strap comprises a first end and a second end that are both attached to the external surface of the sleeve, further wherein a central portion of the strap is unattached to the external surface of the sleeve, further wherein the IV catheter tube is placed through the strap; and the sleeve further comprising a substantially flat pocket disposed on external surface, distal from the strap, wherein the pocket comprises a pocket opening, further wherein the distal end of the IV catheter tube is placed into the pocket through the pocket opening; wherein the narrow opening, the strap and the pocket prevent the IV catheter tube from contacting the patient's skin.

The subject invention further discloses a protective sleeve for an external small length of an inserted PICC line, the protective sleeve comprising: a stretchable tubular member having a first end with a first opening, a second end with a second opening, a substantially flat internal surface, a substantially flat external surface, a lumen substantially parallel with the longitudinal axis, wherein the patient's arm is slidably placed within the sleeve through the first opening through the lumen and then through the second opening such that a portion of the arm is contained within the sleeve and extends through both openings, further wherein the sleeve is positioned on the arm over the insertion point of the PICC line; the sleeve further comprising a slit opening between the internal and external surfaces that is positioned proximate to the intravenous needle insertion point, wherein the external small length of the PICC line is placed through the slit opening; the sleeve comprising a substantially flat strap disposed on the external surface, distal from the slit opening, wherein the strap comprises a first end and a second end that are both attached to the external surface of the sleeve, further wherein a central portion of the strap is unattached to the external surface of the sleeve, wherein the external small length of the PICC line is placed through the strap; and the sleeve further comprising a substantially flat pocket disposed on external surface, distal from the strap, wherein the pocket comprises a pocket opening, further wherein the distal end of the external small length of the PICC line is placed into the pocket through the pocket opening; wherein the slit opening, the strap and the pocket secure the external small length of the PICC line to the sleeve and the patient's arm.

The subject invention discloses a protective sleeve for an external small length of a PICC line extending from an insertion point in a patient's arm, the protective sleeve comprising: a stretchable tubular housing having a proximal end, a distal end, a substantially flat internal surface, a substantially flat external surface, an internal cavity passing through the proximal end to define a proximal opening, and further passing through the distal end to define a distal opening, wherein the patient's arm is slidably placed within the sleeve through the distal opening through the cavity and then through the proximal opening such that a portion of the arm is contained within the sleeve and extends through both openings, further wherein the sleeve is positioned on the arm over the insertion point; the sleeve further comprising a narrow opening between the internal and external surfaces that is positioned proximate to the insertion point, wherein the external small length of the PICC line is placed through the narrow opening; the sleeve comprising a substantially flat strap disposed on the external surface, distal from the narrow opening, wherein the strap comprises a first end and a second end that are both attached to the external surface of the sleeve, further wherein a central portion of the strap is unattached to the external surface of the sleeve, wherein the external small length of the PICC line is placed through the strap; and the sleeve further comprising a substantially flat pocket disposed on external surface, distal from the strap, wherein the pocket comprises a pocket opening, further wherein the distal end of the external small length of the PICC line is placed into the pocket through the pocket opening; wherein the narrow opening, the strap and the pocket prevent the external small length of the PICC line from contacting the patient's skin.

The subject invention also discloses a protective sleeve for an external small length of an inserted PICC line, the protective sleeve comprising: a stretchable cylindrical housing having a first end with a first opening, a second end with a second opening, a substantially flat internal surface, a substantially flat external surface, a lumen substantially parallel with the longitudinal axis, wherein the patient's arm is slidably placed within the sleeve through the first opening through the lumen and then through the second opening such that a portion of the arm is contained within the sleeve and extends through both openings, further wherein the sleeve is positioned on the arm over the insertion point of the PICC line; the sleeve further comprising a slit opening between the internal and external surfaces that is positioned proximate to the intravenous needle insertion point, wherein the slit opening is configured to removably hold the external small length of the PICC line, further wherein the external small length of the PICC line is placed through the slit opening; the sleeve comprising a substantially flat strap disposed on the external surface, distal from the slit opening, wherein the strap comprises a first end and a second end that are both attached to the external surface of the sleeve, further wherein a central portion of the strap is unattached to the external surface of the sleeve, wherein the strap is configured to removably hold the external small length of the PICC line, further wherein the external small length of the PICC line is placed through the strap; and the sleeve further comprising a substantially flat pocket disposed on external surface, distal from the strap, wherein the pocket comprises a pocket opening, wherein the pocket is configured to removably hold the external small length of the PICC line, further wherein the distal end of the external small length of the PICC line is placed into the pocket through the pocket opening; wherein the slit opening, the strap and the pocket immobilize the external small length of the PICC line to the sleeve and the patient's arm.

The subject invention discloses a method of protecting a short length IV catheter tube in a patient's arm, comprising the steps of: inserting the catheter into a patient's vein near an elbow, the catheter attached to the short length IV catheter tube; covering the insertion site with a bandage; sliding a sleeve over the patient's arm, wherein the sleeve comprises a stretchable tubular member having a proximal end, a distal end, a substantially flat internal surface, a substantially flat external surface, an internal cavity passing through the proximal end to define a proximal opening, and further passing through the distal end to define a distal opening, wherein the patient's arm is slidably placed within the sleeve through the distal opening through the cavity and then through the proximal opening such that a portion of the arm is contained within the sleeve and extends through both openings; positioning the sleeve on the patient's arm over the insertion point; placing the short length IV catheter tube through a narrow opening on the sleeve between the internal and external surfaces; placing the short length IV catheter tube through a substantially flat strap disposed on the external surface of the sleeve, distal from the narrow opening, wherein the strap comprises a first end and a second end that are both attached to the external surface of the sleeve, further wherein a central portion of the strap is unattached to the external surface of the sleeve; placing the distal end of the short length IV catheter tube into a substantially flat pocket disposed on external surface of the sleeve, distal from the strap, wherein the narrow opening, the strap and the pocket prevent the IV catheter tube from contacting the patient's skin; and removing the distal end of the short length IV catheter tube whenever necessary for administration of medication or nutrients into the tube.

The subject invention further discloses a method of protecting an external small length of an inserted PICC line, comprising the steps of: inserting the PICC line into a patient's vein near an elbow; covering the insertion site with a bandage; sliding a sleeve over the patient's arm, wherein the sleeve comprises a stretchable cylindrical housing having a first end with a first opening, a second end with a second opening, a substantially flat internal surface, a substantially flat external surface, a lumen substantially parallel with the longitudinal axis, wherein the patient's arm is slidably placed within the sleeve through the first opening through the lumen and then through the second opening such that a portion of the arm is contained within the sleeve and extends through both openings; positioning the sleeve on the patient's arm over the insertion point; placing the PICC line through a slit opening on the sleeve between the internal and external surfaces; placing the PICC line through a substantially flat strap disposed on the external surface of the sleeve, distal from the slit opening, wherein the strap comprises a first end and a second end that are both attached to the external surface of the sleeve, further wherein a central portion of the strap is unattached to the external surface of the sleeve; placing the distal end of the PICC line into a substantially flat pocket disposed on external surface of the sleeve, distal from the strap, wherein the slit opening, the strap and the pocket secure the external small length of the PICC line to the sleeve and the patient's arm; and removing the distal end of the PICC line whenever necessary for administration of medication or nutrients.

The subject invention also discloses a method of protecting an external small length of an inserted PICC line, comprising the steps of: inserting the PICC line into a patient's vein near an elbow; covering the insertion site with a bandage; sliding a sleeve over the patient's arm, wherein the sleeve comprises a stretchable tubular housing having a proximal end, a distal end, a substantially flat internal surface, a substantially flat external surface, an internal cavity passing through the proximal end to define a proximal opening, and further passing through the distal end to define a distal opening, wherein the patient's arm is slidably placed within the sleeve through the distal opening through the cavity and then through the proximal opening such that a portion of the arm is contained within the sleeve and extends through both openings; positioning the sleeve on the patient's arm over the insertion point; placing the PICC line through a narrow opening on the sleeve between the internal and external surfaces; placing the PICC line through a substantially flat strap disposed on the external surface of the sleeve, distal from the slit opening, wherein the strap comprises a first end and a second end that are both attached to the external surface of the sleeve, further wherein a central portion of the strap is unattached to the external surface of the sleeve; placing the distal end of the PICC line into a substantially flat pocket disposed on external surface of the sleeve, distal from the strap, wherein the narrow opening, the strap and the pocket prevent the external small length of the PICC line from contacting the patient's skin; and removing the distal end of the PICC line whenever necessary for administration of medication or nutrients.

In embodiments of the subject invention, the protective sleeve may apply inward compression force that is substantially applied over the internal surface of the sleeve to the patient's arm without inhibiting circulation of the patient's arm. In further embodiments of the subject invention, the protective sleeve may apply inward compression force to the patient's arm such that the compression force maintains that sleeve on the patient's arm and secures either the short length of tube extends from the intravenous needle, the IV catheter tube, or external small length of the PICC line without any additional fasteners. In other embodiments of the subject invention, the protective sleeve does not contain a fastener selected from the group consisting of hook and loop fasteners, buttons, clamps, brackets, buckles, magnets, snaps, tie straps, tape layers, or adhesives.

In further embodiments of the subject invention, the protective sleeve may apply inward compression force that is substantially applied over the internal surface of the sleeve to the patient's arm without inhibiting circulation of the patient's arm. In even further embodiments of the subject invention, the protective sleeve may apply inward compression force to the patient's arm such that the compression force maintains that sleeve on the patient's arm and secures either the short length of tube extends from the intravenous needle, the IV catheter tube, or external small length of the PICC line without any additional fasteners. In other embodiments of the subject invention, the protective sleeve does not contain a fastener selected from the group consisting of hook and loop fasteners, buttons, clamps, brackets, buckles, magnets, snaps, tie straps, tape layers, or adhesives.

In additional embodiments of the subject invention, the slit opening, the strap and the external pocket all comprise a stretchability that applies sufficient compression force for holding and securing either the external small length of the PICC line and the distal end cap, the capped IV catheter tube, or the short length of tube extending from the intravenous needle, such that this compression force does not substantially affect circulation in the patient's arm, and keeps these tubes in place during treatment, during sleep, and during normal activities.

In embodiments of the subject invention, the protective sleeve may be a continuous tubular member or cylindrical housing that must be slid or rolled onto the patient's arm. In further embodiments of the subject invention, the substantially flat member or the substantially flat member of the sleeve may comprise a unitary piece.

In additional embodiments of the subject invention, the protective sleeve may have a substantially equal diameter from the first end to the second end. In further embodiments of the subject invention, the protective sleeve may have a substantially equal diameter from the proximal end to the distal end.

In other embodiments of the subject invention, the protective sleeve may have a tapering diameter from the first end to the second end. In further embodiments of the subject invention, the protective sleeve may have a tapering diameter from the proximal end to the distal end.

In additional embodiments of the subject invention, the cross-sectional shape of the sleeve may be selected from the group consisting of substantially circular or substantially elliptical.

In embodiments of the subject invention, the sleeve may be worn on either arm.

In further embodiments of the subject invention, the sleeve may further comprise a flexible substantially transparent or semi-transparent window that traverses the external and internal surfaces of the sleeve. In these embodiments, the sleeve should be positioned on the patient's arm such that the flexible substantially transparent or semi-transparent window is over the PICC line or intravenous needle insertion point. In another embodiment of the subject invention, this substantially transparent window may be a mesh material.

In embodiments of the subject invention, the slit opening, the strap and the external pocket may all be substantially parallel with each other.

In further embodiments of the subject invention, the protective sleeve, the strap and the external pocket may all be composed of a slightly flexible and lightweight fabric that stretches over a patient's arm and is non-irritating to the skin. In these embodiments of the subject invention, this fabric may be selected from the group consisting of natural fibers, such as cottons, wools, silks, twills, cloths and bamboo; man-made fibers such as polyesters, nylons, tencels, viscose; or any combination of natural or man-made fibers and weaves.

The subject invention discloses a chest wrap for a central venous catheter inserted into a vein in a patient's chest, wherein the short length of tube extends from the central venous catheter and comprises a cap on a distal end, the chest wrap comprising: a stretchable substantially flat having a first end with a first fastener, a second end with a second fastener, a substantially flat internal surface, a substantially flat external surface, an internal lumen between the internal surface and the external surface, wherein the chest wrap is wrapped around a patient's chest and the first fastener is attached to the second fastener to form a loop such that a portion of the chest is contained within the looped chest wrap, further wherein the chest wrap is positioned on the chest over the insertion point of the central venous catheter; the chest wrap further comprising a first slit opening between the internal surface and the internal lumen that is positioned proximate to the central venous catheter insertion point, wherein the tube extending from the central venous catheter is placed through the first slit opening into the internal lumen, further wherein the tube extending from the central venous catheter is wrapped around the chest of the patient; the chest wrap further comprising a second slit opening between the internal lumen and the external surface, wherein the tube extending from the central venous catheter is placed through the second slit opening onto the external surface; the chest wrap further comprising a third slit opening between the external surface and the internal lumen, wherein the tube extending from the central venous catheter is placed through the third slit opening into the internal lumen; the chest wrap further comprising a substantially flat strap disposed on the external surface, wherein the strap comprises a first end and a second end that are both attached to the external surface of the chest wrap, further wherein a central portion of the strap is unattached to the external surface of the chest wrap, further wherein the tube extending from the central venous catheter is placed through the strap within the internal lumen; wherein the first, second and third slit openings, and the strap secure the tube extending from the central venous catheter to the chest wrap and the patient's chest.

The subject invention also discloses a chest wrap for a Broviac catheter inserted into a vein in a patient's chest, wherein the short length of tube extends from the Broviac catheter and comprises a cap on a distal end, the chest wrap comprising: a stretchable substantially flat having a first end with a first fastener, a second end with a second fastener, a substantially flat internal surface, a substantially flat external surface, an internal lumen between the internal surface and the external surface, wherein the chest wrap is wrapped around a patient's chest and the first fastener is attached to the second fastener to form a loop such that a portion of the chest is contained within the looped chest wrap, further wherein the chest wrap is positioned on the chest over the insertion point of the Broviac catheter; the chest wrap further comprising a first slit opening between the internal surface and the internal lumen that is positioned proximate to the Broviac catheter insertion point, wherein the tube extending from the Broviac catheter is placed through the first slit opening into the internal lumen, further wherein the tube extending from the Broviac catheter is wrapped around the chest of the patient; the chest wrap further comprising a second slit opening between the internal lumen and the external surface, wherein the tube extending from the Broviac catheter is placed through the second slit opening onto the external surface; the chest wrap further comprising a third slit opening between the external surface and the internal lumen, wherein the tube extending from the Broviac catheter is placed through the third slit opening into the internal lumen; the chest wrap further comprising a substantially flat strap disposed on the external surface, wherein the strap comprises a first end and a second end that are both attached to the external surface of the chest wrap, further wherein a central portion of the strap is unattached to the external surface of the chest wrap, further wherein the tube extending from the Broviac catheter is placed through the strap within the internal lumen; wherein the first, second and third slit openings, and the strap secure the tube extending from the Broviac catheter to the chest wrap and the patient's chest.

The subject invention further discloses a method of protecting a central venous catheter in a patient's chest, comprising the steps of: inserting the catheter into a patient's vein in the chest, the catheter attached to a short length tube; covering the insertion site with a bandage; wrapping a chest wrap over the patient's chest, wherein the chest wrap comprises a stretchable substantially flat member having a first end with a first fastener, a second end with a second fastener, a substantially flat internal surface, a substantially flat external surface, an internal lumen between the internal surface and the external surface, wherein the chest wrap is wrapped around a patient's chest and the first fastener is attached to the second fastener to form a loop such that a portion of the chest is contained within the looped chest wrap; positioning the chest wrap on the patient's chest over the insertion point; placing the tube extending from the central venous catheter through a first slit opening between the internal surface and the internal lumen; wrapping the tube extending from the central venous catheter around the chest of the patient; placing the tube extending from the central venous catheter through a second slit opening between the internal lumen and the external surface; placing the tube extending from the central venous catheter through a third slit opening between the external surface and the internal lumen; placing the distal end of the tube extending from the central venous catheter through a substantially flat strap disposed on the external surface, wherein the strap comprises a first end and a second end that are both attached to the external surface of the chest wrap, further wherein a central portion of the strap is unattached to the external surface of the chest wrap, further wherein the tube extending from the central venous catheter is placed through the strap within the internal lumen, wherein the first, second, third slit openings, and the strap secure the tube extending from the central venous catheter to the chest wrap and the patient's chest; and removing the distal end of the tube extending from the central venous catheter whenever necessary for administration of medication or nutrients into the tube.

The subject invention further discloses a method of protecting a Broviac catheter in a patient's chest, comprising the steps of: inserting the catheter into a patient's vein in the chest, the catheter attached to a short length tube; covering the insertion site with a bandage; wrapping a chest wrap over the patient's chest, wherein the chest wrap comprises a stretchable substantially flat member having a first end with a first fastener, a second end with a second fastener, a substantially flat internal surface, a substantially flat external surface, an internal lumen between the internal surface and the external surface, wherein the chest wrap is wrapped around a patient's chest and the first fastener is attached to the second fastener to form a loop such that a portion of the chest is contained within the looped chest wrap; positioning the chest wrap on the patient's chest over the insertion point; placing the tube extending from the Broviac catheter through a first slit opening between the internal surface and the internal lumen; wrapping the tube extending from the Broviac catheter around the chest of the patient; placing the tube extending from the Broviac catheter through a second slit opening between the internal lumen and the external surface; placing the tube extending from the Broviac catheter through a third slit opening between the external surface and the internal lumen; placing the distal end of the tube extending from the Broviac catheter through a substantially flat strap disposed on the external surface, wherein the strap comprises a first end and a second end that are both attached to the external surface of the chest wrap, further wherein a central portion of the strap is unattached to the external surface of the chest wrap, further wherein the tube extending from the Broviac catheter is placed through the strap within the internal lumen, wherein the first, second, third slit openings, and the strap secure the tube extending from the Broviac catheter to the chest wrap and the patient's chest; and removing the distal end of the tube extending from the Broviac catheter whenever necessary for administration of medication or nutrients into the tube.

In embodiments of the subject invention, the chest wrap may apply inward compression force that is substantially applied over the internal surface of the chest wrap to the patient's chest without inhibiting circulation of the patient's chest. In further embodiments of the subject invention, the chest wrap may apply inward compression force to the patient's chest such that the compression force maintains that chest wrap on the patient's chest and secures either the central venous catheter or the Broviac catheter without any additional fasteners. In other embodiments of the subject invention, the first and second fasteners may be selected from the group consisting of hook and loop fasteners, buttons, clamps, brackets, buckles, magnets, snaps, tie straps, tape layers, or adhesives.

In further embodiments of the subject invention, the substantially flat member of the chest wrap may comprise a unitary piece.

In additional embodiments of the subject invention, the chest wrap may have a substantially equal width from the first end to the second end. In other embodiments of the subject invention, the chest wrap may have a tapering width from the first end to the second end.

In other embodiments of the subject invention, the chest wrap may further comprise a flexible substantially transparent or semi-transparent window that traverses the external and internal surfaces of the chest wrap. In these embodiments, the chest wrap should be positioned on the patient's chest such that the flexible substantially transparent or semi-transparent window is over the Broviac catheter or central venous catheter insertion point. In another embodiment of the subject invention, this substantially transparent window may be a mesh material.

In even further embodiments of the subject invention, the chest wrap and the strap may all be composed of a slightly flexible and lightweight fabric that stretches over a patient's chest and is non-irritating to the skin. In these embodiments of the subject invention, this fabric may be selected from the group consisting of natural fibers, such as cottons, wools, silks, twills, cloths and bamboo; man-made fibers such as polyesters, nylons, tencels, viscose; or any combination of natural or man-made fibers and weaves.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

DETAILED DESCRIPTION OF THE EMBODIMENTS

Figure 1:
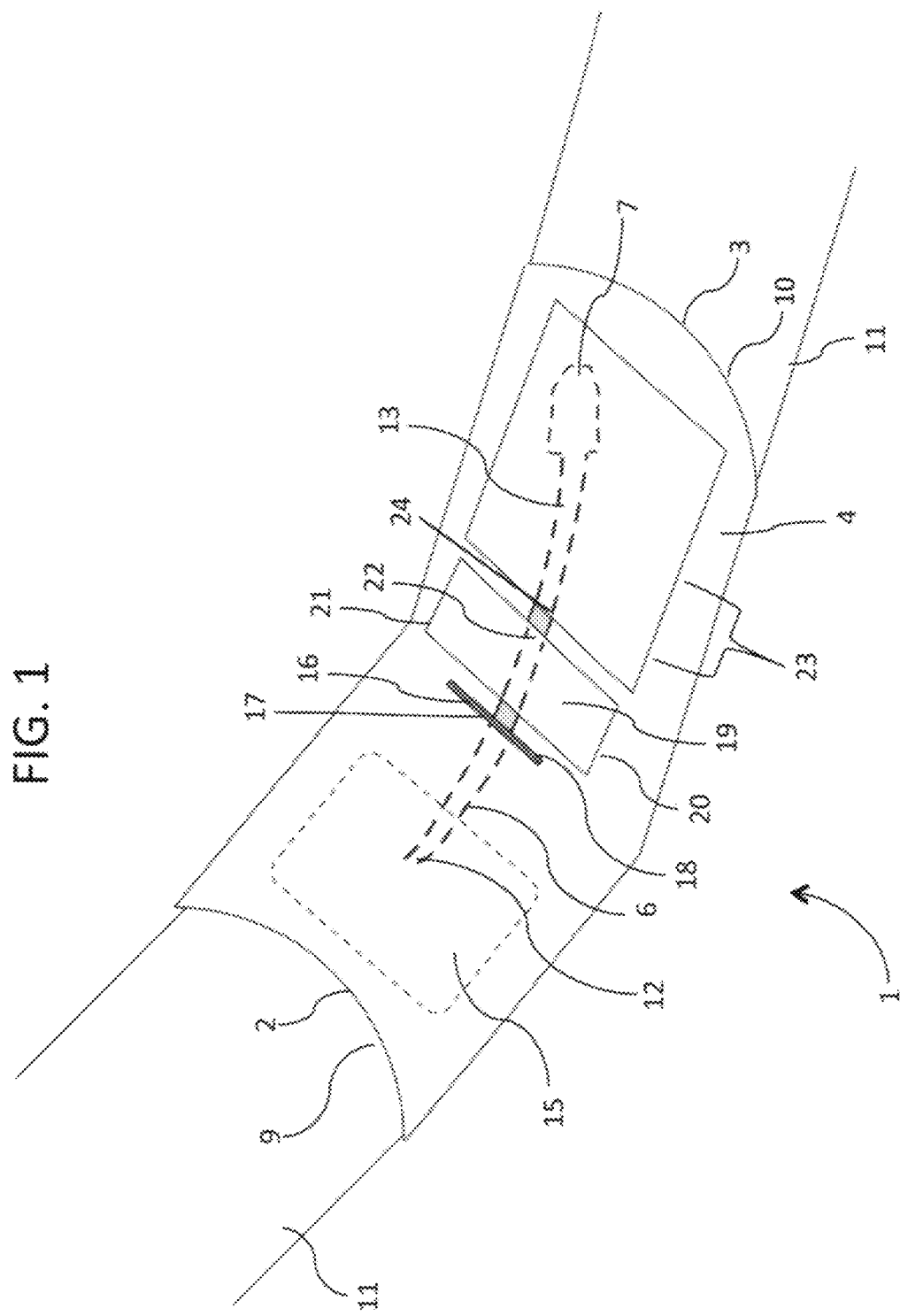
FIG. 1 illustrates a perspective view of the stretchable sleeve placed over a patient's arm with a single tube lumen secured by the sleeve.

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

FIGS. 1-4 illustrate a stretchable arm sleeve 1 of the subject invention. The sleeve 1 is a continuous tubular, or cylindrical, structure with a longitudinal axis, a proximal end 2, a distal end 3, a substantially flat external surface 4 and a substantially flat internal surface 5. The external 4 and internal surfaces 5 of the sleeve 1 are substantially smooth and clean, other than the additional components described herein. These substantially smooth surfaces reduce any protrusions that may catch, snag, pull, or push any portion of the external short length of the PICC line 6 and its end cap 7 that are to be secured by the sleeve 1.

The sleeve 1 contains a lumen 8, or internal cavity that is substantially parallel with the longitudinal axis. The lumen 8 passes through the proximal end 2 to define a proximal opening 9 that is substantially perpendicular to the longitudinal axis, and further passes through the distal end 3 to define a distal opening 10 that is substantially perpendicular to the longitudinal axis. The proximal opening 9, the distal opening 10, and the lumen 8 are all configured for receiving and holding a patient's arm 11. In use, a patient places his or her arm 11 through the proximal opening 9, through the lumen 8 and out through the distal opening 10 to place the sleeve 1 over the PICC line insertion point 12 on the arm 11.

In one embodiment of the subject invention, the sleeve 1 may have a substantially equal diameter from the proximal end 2 to the distal end 3. In another embodiment of the subject invention, the sleeve 1 may have slightly taped diameter from the proximal end 2 to the distal end 3. This slightly tapered diameter embodiment may be used to accommodate an elbow or forearm that has a larger diameter than a wrist on the same arm.

In embodiments of the subject invention, the cross-sectional shape of the sleeve 1 may be substantially circular or substantially elliptical.

The sleeve 1 comprises is stretchable so as to allow the sleeve 1 to be easily slipped on and off a patient's arm 11. This stretchability should apply sufficient inward compression force such that the sleeve 1 should substantially conform to the anatomy of a patient's arm 11, such that compression force of the sleeve 1 does not substantially affect circulation in the limb, remains in place during treatment, remains in place while the patient sleeps, and remains in place if the patient moves or engages in normal activities. This compression force should be inward compression that is substantially equal over the internal surface 5 of the sleeve 1. The sleeve 1 comprises a stretchability that allows it to remain in place on the patient's arm and secure the PICC line 6 in place without any additional fasteners, such as hook and loop fasteners, buttons, clamps, brackets, buckles, magnets, snaps, tie straps, tape layers, or adhesives.

This sleeve 1 must also allow the patient freedom of movement in the covered arm 11. The sleeve 1 is designed for use with all ages and sizes and can be worn on either arm 11.

Figure 2:
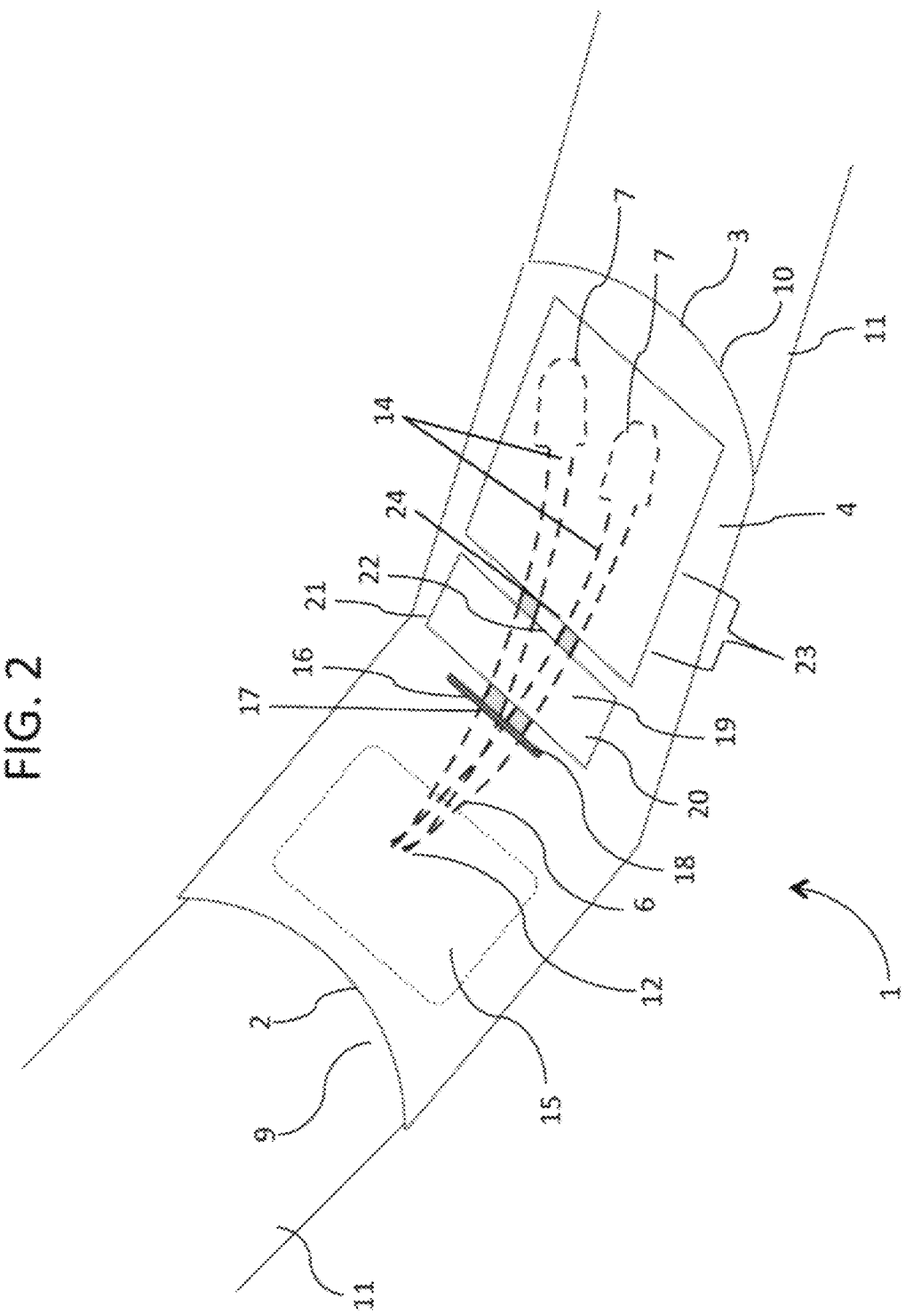
FIG. 2 illustrates a perspective view of the stretchable sleeve placed over a patient's arm with a double tube lumen secured by the sleeve.
Figure 3:
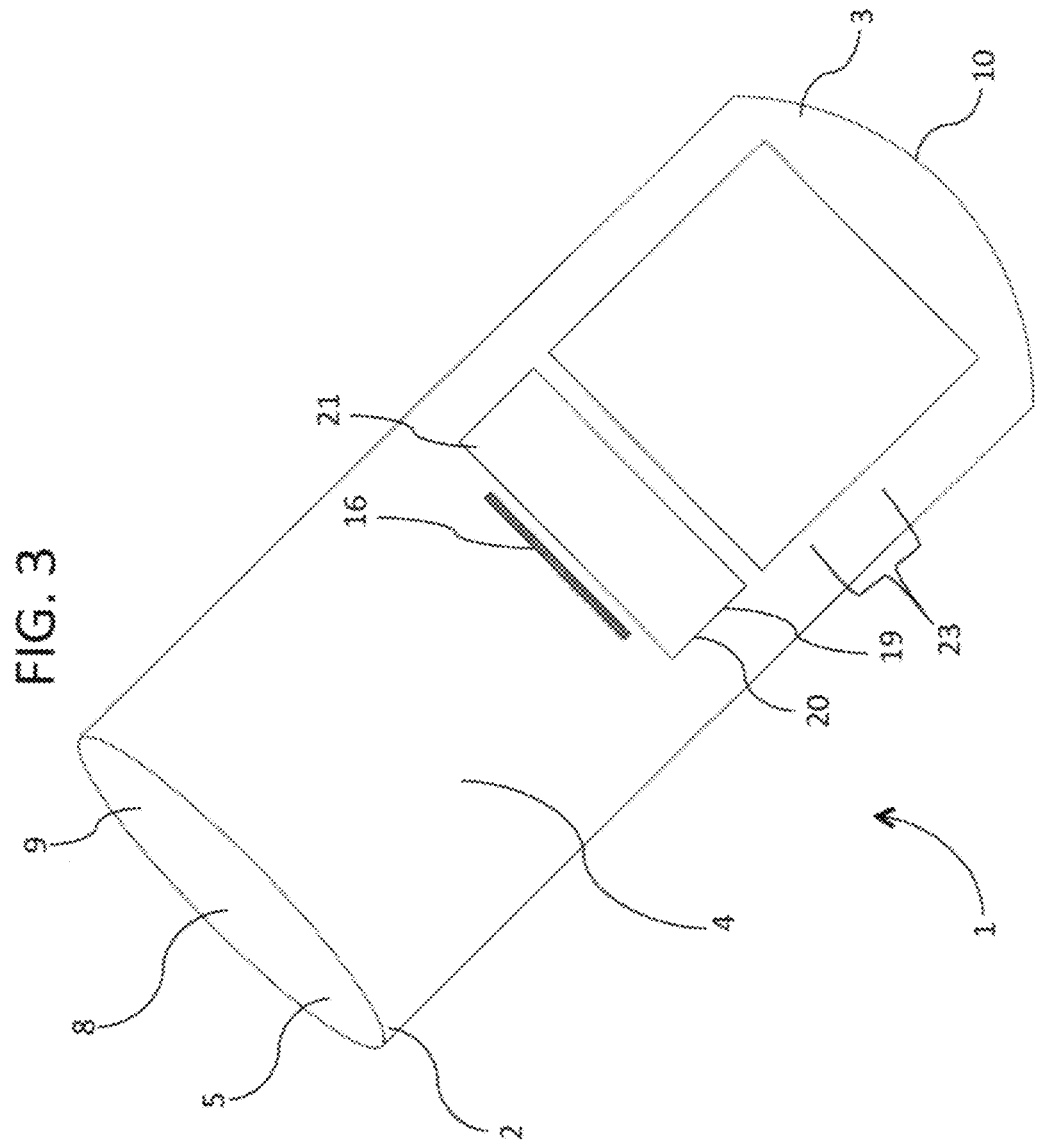
FIG. 3 illustrates a top view of the unattached stretchable sleeve.
Figure 4:
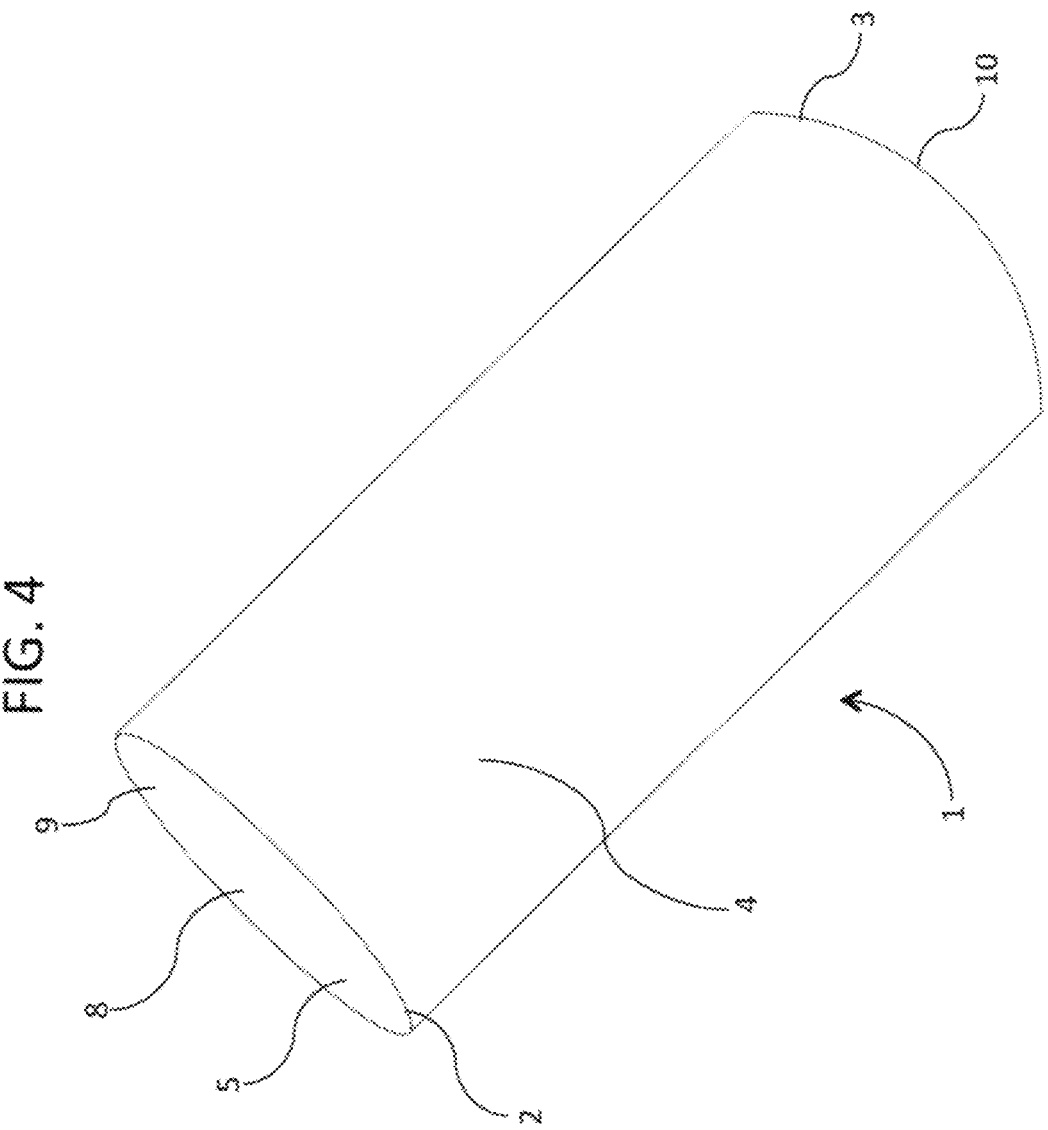
FIG. 4 illustrates a bottom view of the unattached stretchable sleeve.

FIGS. 1 and 2 show the insertion of a peripherally inserted central catheter (PICC line) into the arm of a patient at the site 12 of an internal vein. The PICC line 6 uses a plastic tube with one or more internal lumens as a means of administering liquid medications or nutrients to the patient. These PICC lines 6 allow intravenous therapies to continue for prolonged period of times.

Once the PICC line is inserted, a small length of the PICC line 6 remains external to the patient, extending outwards from the point of insertion 12. The external end of the PICC line 6 is capped 7 to prevent bacteria, viruses or contaminants from entering the PICC line. As shown in FIG. 1, the small length of PICC line 6 may be one tube 13 for a single internal lumen. As shown in FIG. 2, the small length of PICC line may include two tubes 14 for a double internal lumen.

The end of the small length of the PICC line 6 contains a cap 7. This cap 7 must be periodically replaced, typically weekly, to reduce the risk of contamination. Replacing the cap 7 must also be a sterile procedure that is conducted with washed hands, sterile gloves, sterile clothing, and alcohol swaps in a sterile environment.

The insertion point 12 of the PICC line 6 may be covered with a traditional removable bandage 15. In this embodiment, this removable bandage 15 should only cover a very small portion of the external small length of the PICC line 6 that is proximate to the insertion point 12.

In one embodiment of the subject invention, the sleeve 1 may comprise a flexible substantially transparent or semi-transparent window (not shown) that traverses the external 4 and internal surfaces 5 of the sleeve 1. The sleeve 1 should be aligned over the patient's arm 11 such that the flexible substantially transparent or semi-transparent window is over the PICC line insertion point 12. In another embodiment of the subject invention, this substantially transparent window may be composed of a mesh or mesh-like material.

The sleeve 1 is designed to cover and protect both the arm 11 and external short length of the PICC line 6. The sleeve covers the PICC line insertion area 12 and protects it from clothing, rubbing, and other external influences.

The sleeve 1 comprises a slit opening 16 proximate to the PICC line insertion point 12. This slit opening 16 passes through the internal surface 5 to define an internal opening 17 that may be substantially perpendicular to the longitudinal axis and further passes through the external surface 4 to define an external opening 18 that may be substantially perpendicular to the longitudinal axis. The slit opening 16, the internal opening 17, and the external opening 18 are all configured for receiving and removably holding the external small length of the PICC line 6. In use, a patient moves the external small length of the PICC line 6 and the distal end cap 7 through the slit opening 16 onto the exterior surface 4 of the sleeve 1.

The sleeve 1 further comprises a substantially flat strap 19 on the external surface 4, distal from the slit opening 16. This strap 19 comprises a first end 20 and a second end 21 that are both attached to the external surface 4 of the sleeve 1. The strap 19 may be substantially rectangular or square in shape. The central portion of the strap 19 is unattached to the sleeve 1 to form a strap opening 22 that is configured for receiving and removably holding the external small length of the PICC line 6. This strap opening 22 may be substantially perpendicular to the longitudinal axis. In use, a patient moves the external small length of the PICC line 6 and the distal end cap 7, already passed through the slit opening 16, through the strap opening 22 underneath strap 19.

The sleeve 1 further comprises a substantially flat pocket 23, disposed on external surface 4 of the sleeve 1, distal from the strap 19. This pocket 23 comprises a pocket opening 24 that is substantially perpendicular to the longitudinal axis and is configured for receiving and removably holding the external small length of the PICC line 6 and the distal end cap 7. The cap 7 and the external small length of the PICC line 6 are contained in a readily accessible position within the pocket 23 for use during IV treatments. The pocket 23 secures the PICC line cap 7 and protects it from dirt, fingers and other infection risks.

The pocket 23 permits easy accessibility to the PICC line 6 for medical professionals when administering infusion therapies without the need to remove the external small length of the PICC line 6 from the securing strap 19 or slit opening 16.

The slit opening 16, the strap 19 and the external pocket 23 are all substantially parallel with each other. The slit opening 16, the strap 19 and the external pocket 23 are all stretchable such that they apply sufficient compression force for holding the external small length of the PICC line 6 and the distal end cap 7 on the patient's arm 11 such that this force does not substantially affect circulation in the limb, and keeps the external small length of the PICC line 6 in place during treatment, sleep, and normal activities.

The slit opening 16, the strap 19 and the external pocket 23 prevent the external small length of the PICC line 6 and the distal end cap 7 from contacting the patient's skin, eliminating the need for additional medical tape to secure the PICC line 6 or the cap 7. This reduction of medical tape in the dressing reduces skin irritation for the patient.

In embodiments of the subject invention, the sleeve 1, the strap 19 and the external pocket 23 may all be composed of a slightly flexible and lightweight fabric that stretches over a patient's arm 11 and is non-irritating to the skin. In embodiments of the subject invention, this fabric may be natural fibers, such as cottons, wools, silks, twills, cloths and bamboo; man-made fibers such as polyesters, nylons, tencels, viscose; or any combination of natural or man-made fibers and weaves.

FIGS. 5-11 illustrate a stretchable chest wrap 25 of the subject invention for securing and protecting a central venous catheter 26 and/or Broviac line from dislodgement by the patient.

Figure 5:
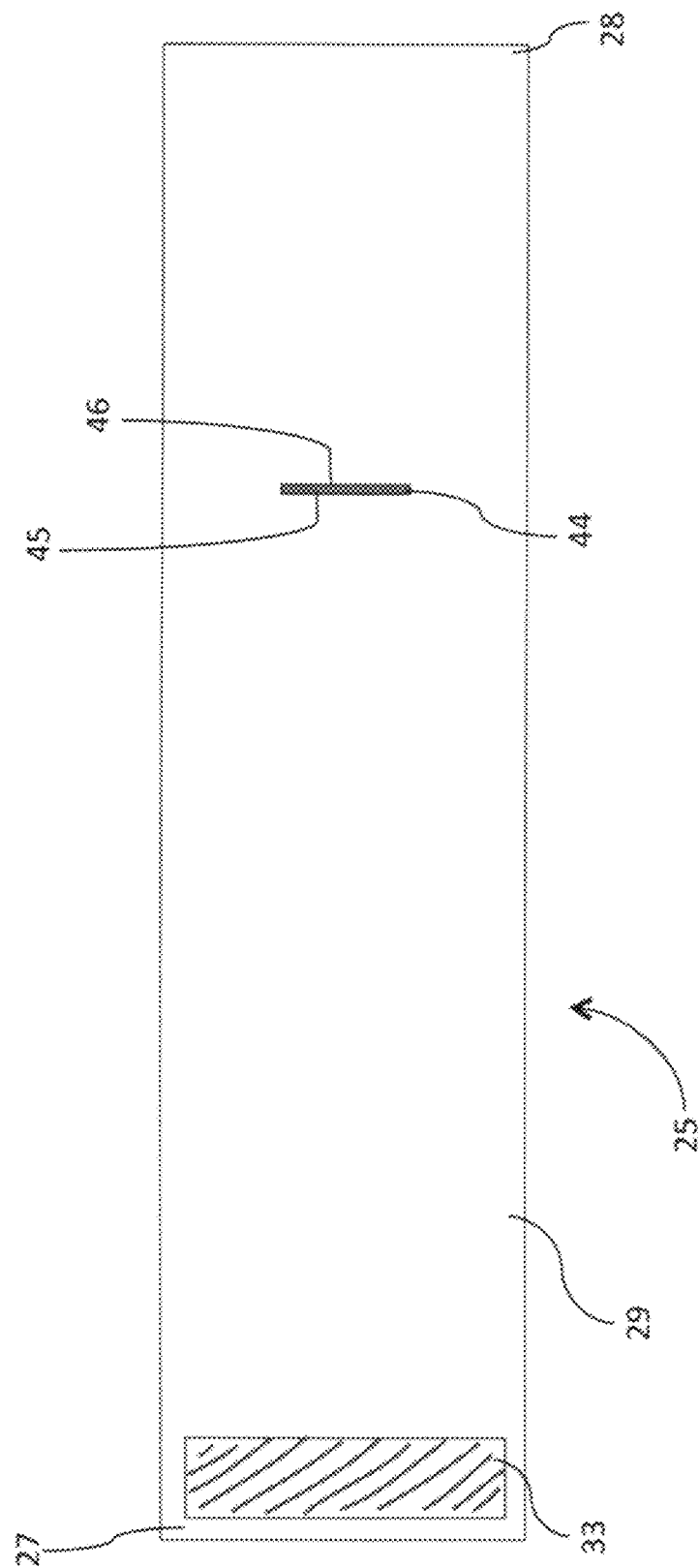
FIG. 5 illustrates a top view of the internal surface of the chest wrap in the unrolled position.
Figure 6:
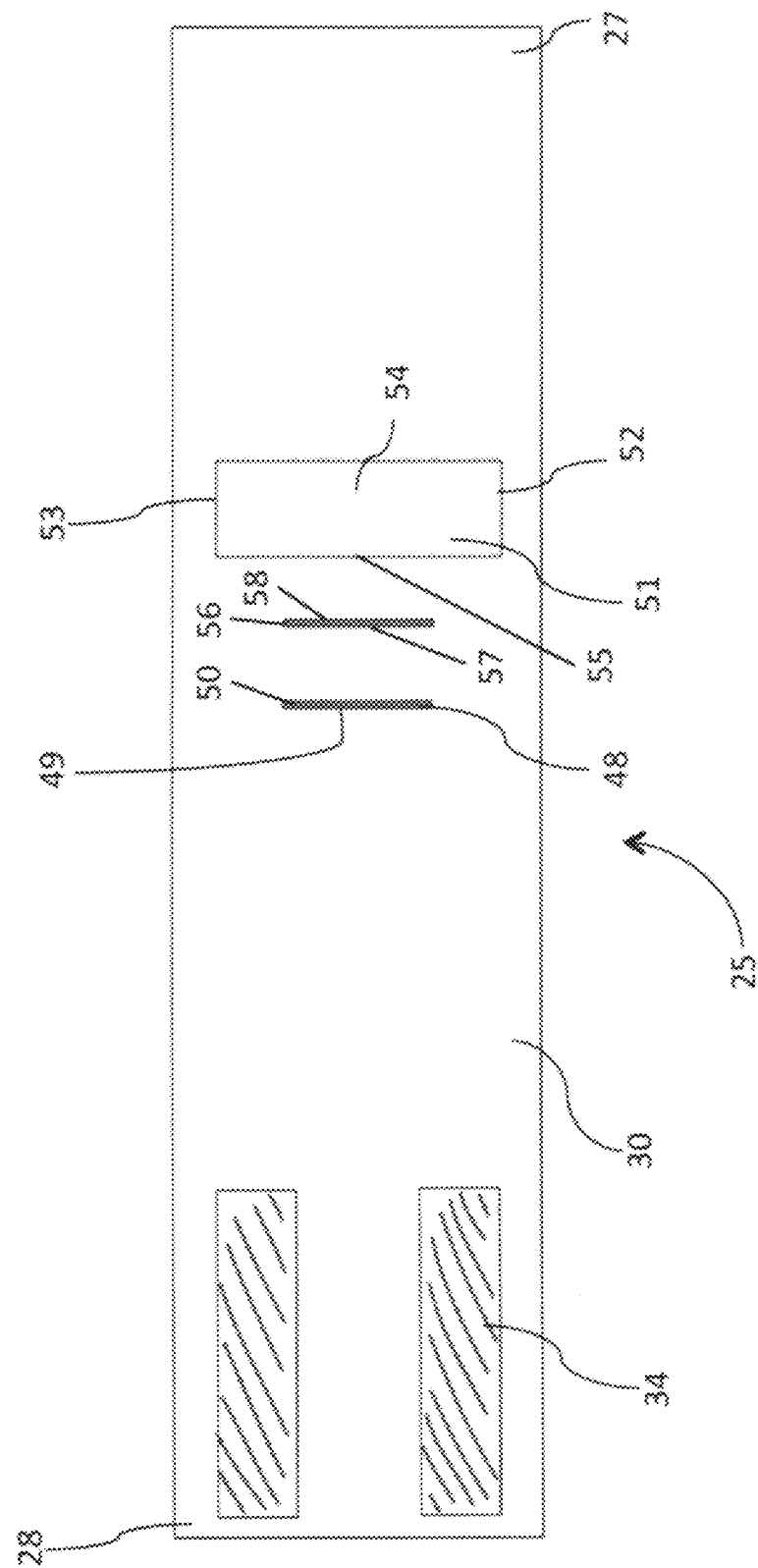
FIG. 6 illustrates a top view of the external surface of the chest wrap in the unrolled position.

The chest wrap 25 is a substantially flat wrap with a first end 27, a second end 28, an internal surface 29, shown in FIG. 5, and an external surface 30, shown in FIG. 6. There is a lumen 47 between the internal surface 29 and the external surface 30. The external 30 and internal surfaces 29 of the chest wrap 25 are substantially smooth and clean, other than the additional components described herein. These substantially smooth surfaces reduce any protrusions that may catch, snag, pull, or push any portion of the external short length of the central venous catheter 31 and its end cap 32 that are to be secured to the chest wrap 25.

Figure 11:
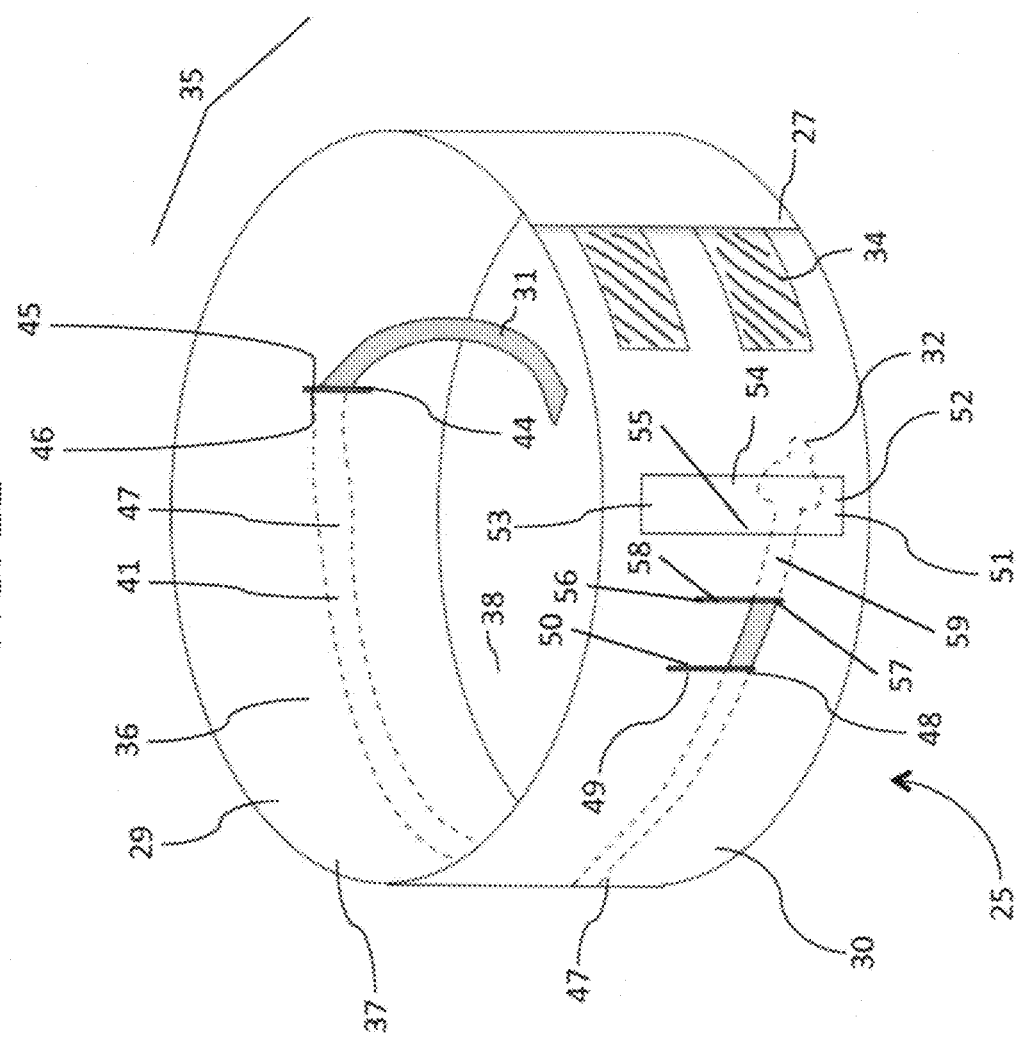
FIG. 11 illustrates a side perspective view of the chest wrap in the rolled position and securing a single tube lumen.

As illustrated in FIG. 5, the internal surface 29 of the chest wrap 25 may comprise a fastener 33 on the first end 27. As illustrated in FIG. 6, the external surface 30 of the chest wrap 25 may contain a second fastener 34 on the second end 28. As illustrated in FIG. 11, the chest wrap may be wrapped into a tubular, cylindrical-shaped, loop 35 with the first end 27 overlapping the second end 28 such that the fastener 33 attaches to fastener 34. In embodiments of the subject invention, fasteners 33 and 34 may include any device which removably attaches first end 27 to the second end 28 to form loop 35. Such fastening means can include, but is not limited to, hook and loop fasteners; hook and eye fasteners; adhesives, including reusable adhesives; adhesive tape; zippers; buttons; snaps; pins; stitching; clamps; and the like.

The looped 35 chest wrap 25 forms a second lumen 36, or internal cavity that is substantially parallel with the longitudinal axis. The lumen 36 defines a top opening 37 that is substantially perpendicular to the longitudinal axis, and further defines a bottom opening 38 that is substantially perpendicular to the longitudinal axis. The top opening 37, the bottom opening 38, and the lumen 36 are all configured for receiving and holding a patient's chest 39. In use, as illustrated in FIGS. 7-10, a patient wraps the chest wrap 25 around the chest 39 over the Central venous catheter insertion point 40 with the first end 27 overlapping the second end 28 such that the fastener 33 attaches to fastener 34.

In one embodiment of the subject invention, the looped 35 chest wrap 25 may have a substantially equal diameter from the top opening 37 to the bottom opening 38.

In another embodiment of the subject invention, the chest wrap 25 may have slightly taped diameter from the top opening 37 to the bottom opening 38. This slightly tapered diameter embodiment may be used to accommodate a larger chest 39.

In embodiments of the subject invention, the cross-sectional shape of the looped 35 chest wrap 25 may be substantially circular or substantially elliptical.

The chest wrap 25 is stretchable so as to allow the chest wrap 25 to be easily slipped on and off a patient's chest 39. This fabric should apply sufficient inward compression force such that the chest wrap 25 should substantially conform to the anatomy of a patient's chest 39, such that compression force of the chest wrap 25 does not substantially affect circulation in the limb, remains in place during treatment, remains in place while the patient sleeps, and remains in place if the patient moves or engages in normal activities. This compression force should be inward compression that is substantially equal over the internal surface 29 of the chest wrap 25. The chest wrap 25 fabric allows it to remain in place on the patient's chest and secure the central venous catheter 31 in place.

Figure 7:
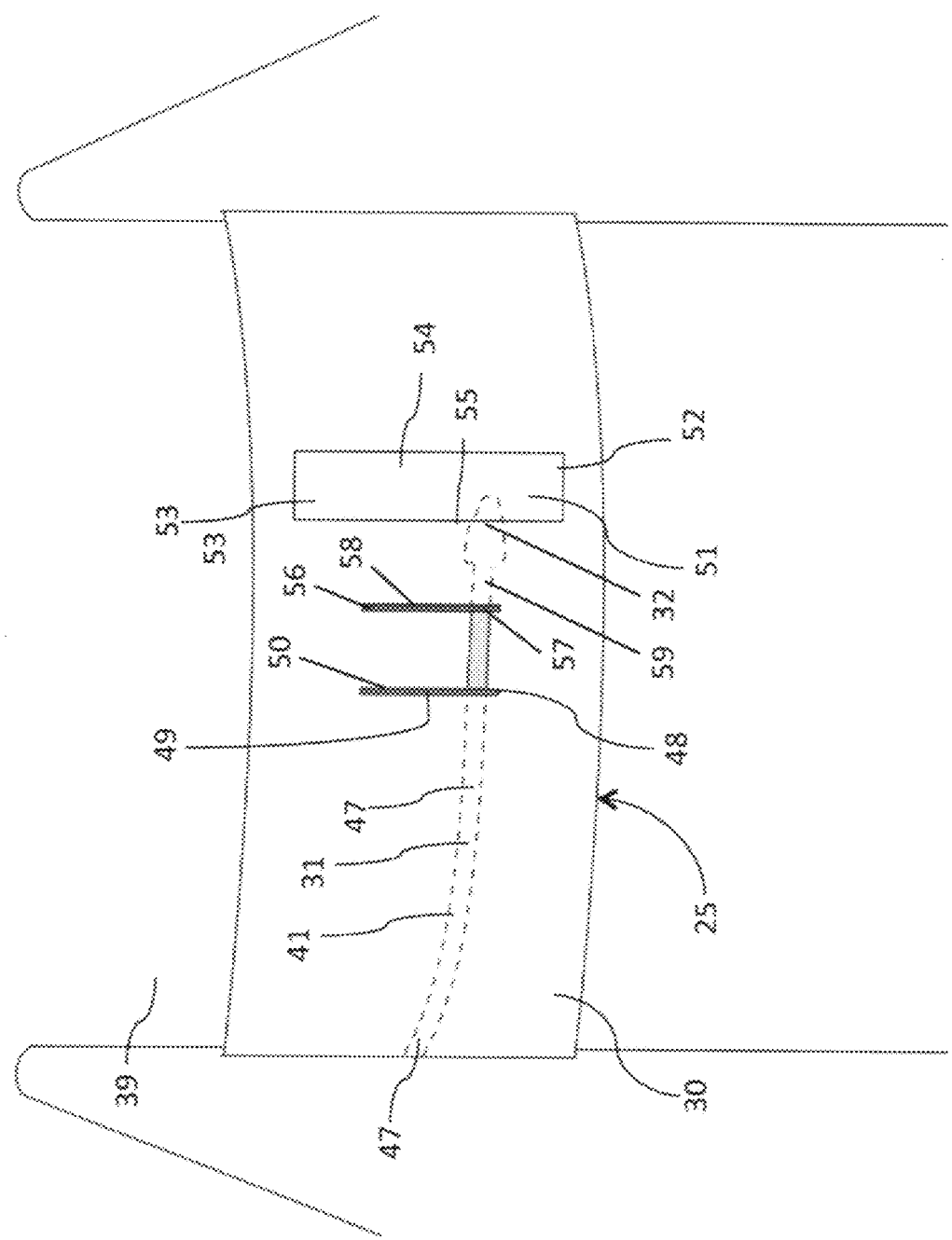
FIG. 7 illustrates a back perspective view of the chest wrap in the rolled position around the chest of a patient and securing a single tube lumen.
Figure 8:
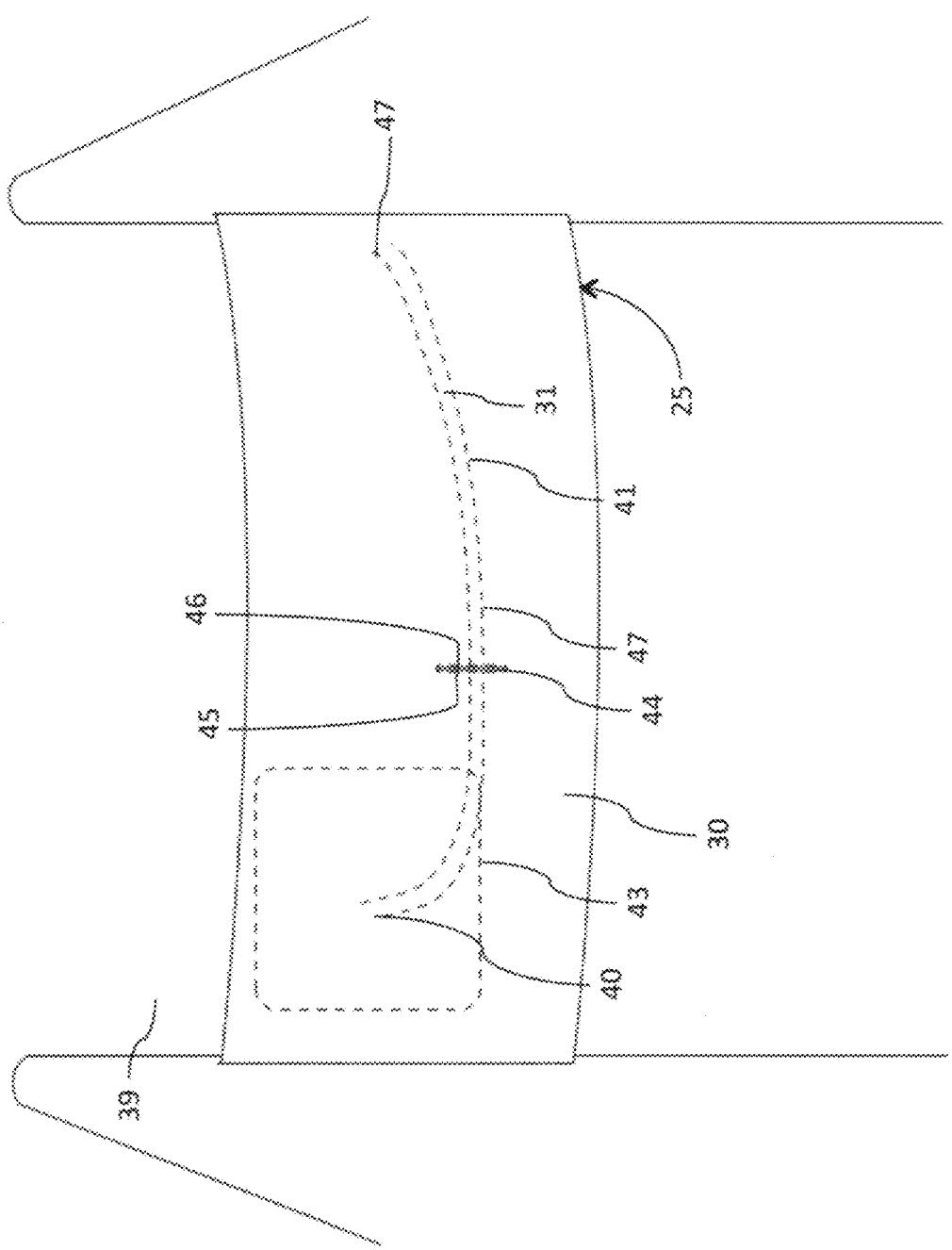
FIG. 8 illustrates a front perspective view of the chest wrap in the rolled position around the chest of a patient and securing a single tube lumen.
Figure 9:
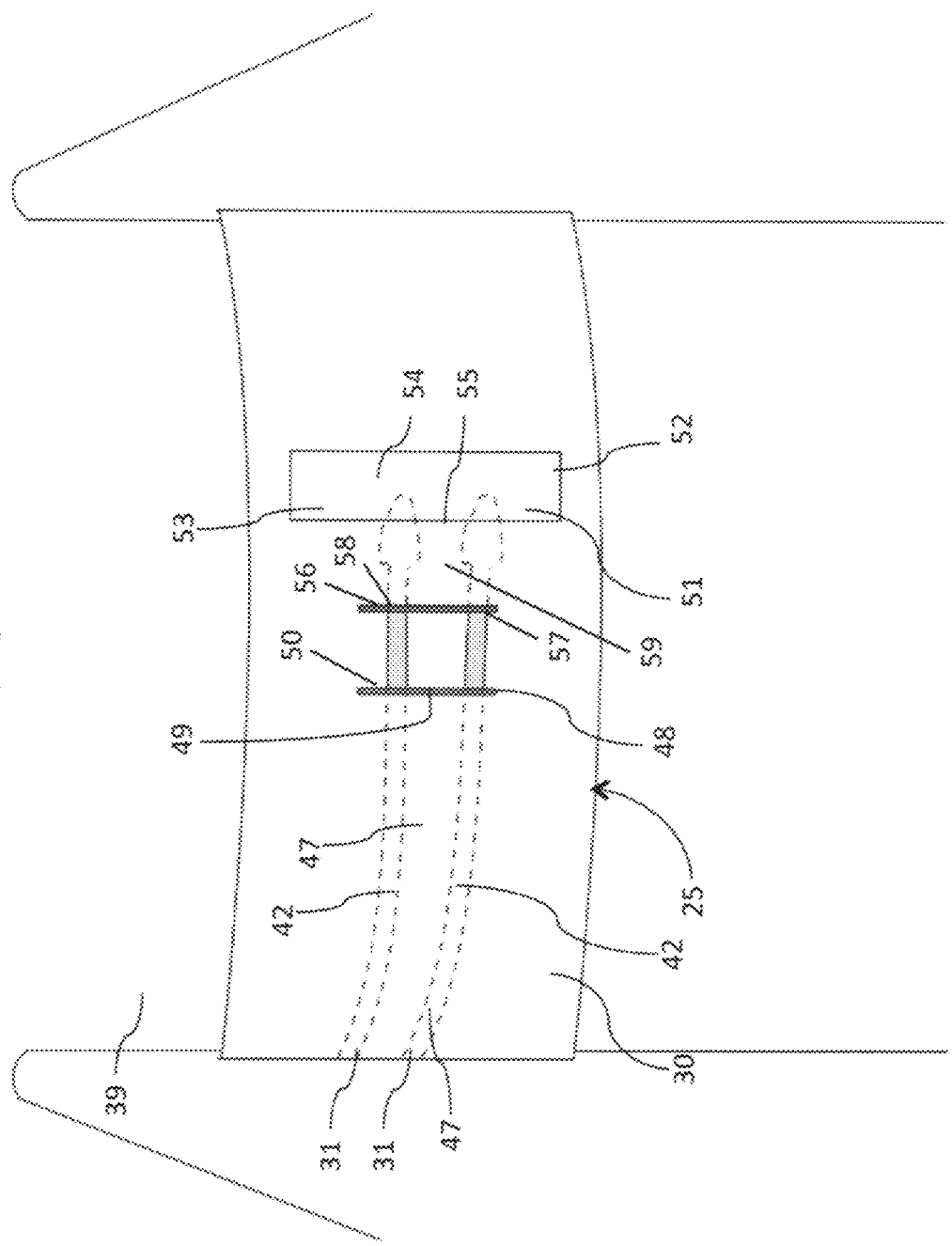
FIG. 9 illustrates a back perspective view of the chest wrap in the rolled position around the chest of a patient and securing a double tube lumen.
Figure 10:
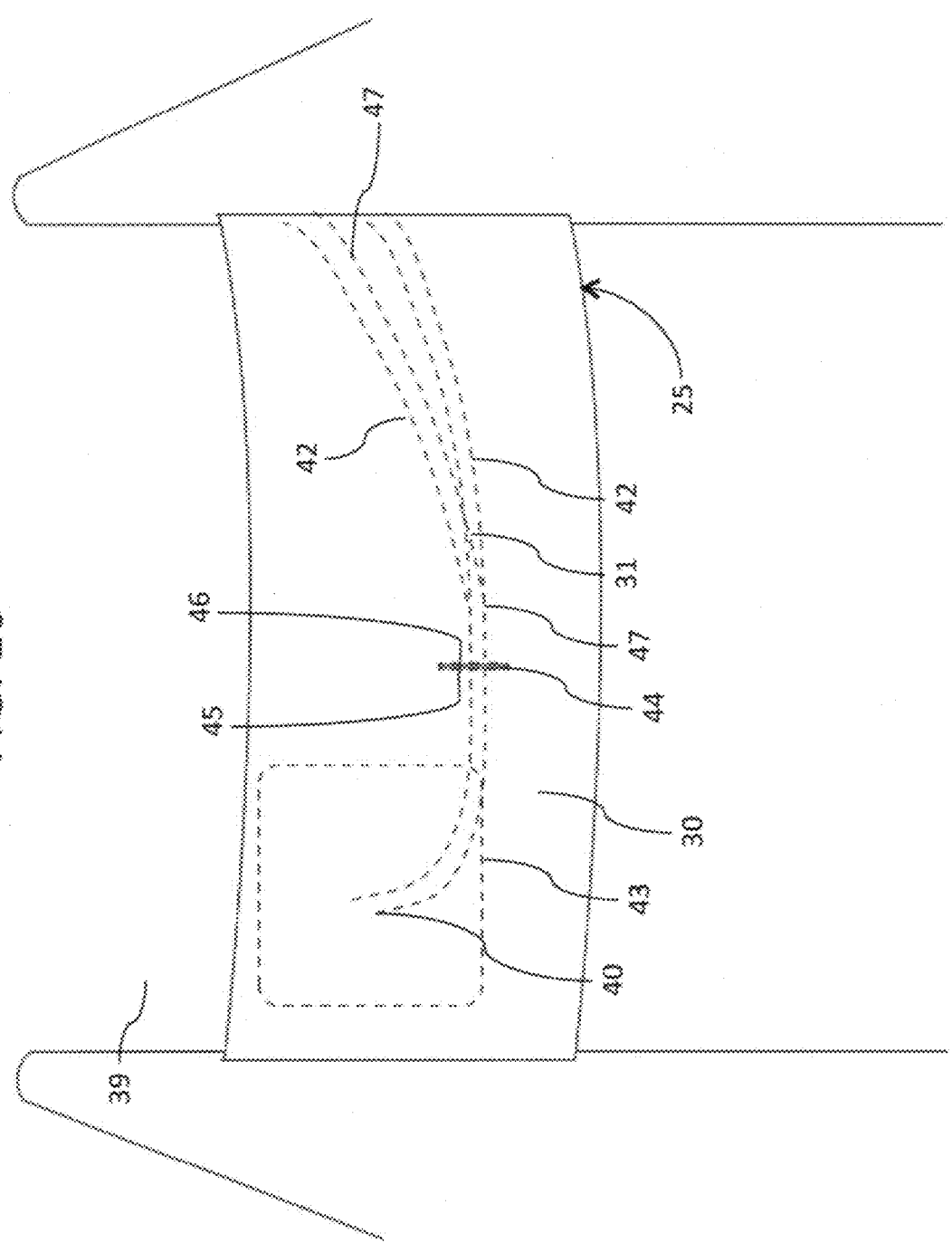
FIG. 10 illustrates a front perspective view of the chest wrap in the rolled position around the chest of a patient and securing a double tube lumen.

FIGS. 8 and 10 show the insertion of a Central venous catheter into the chest 39 of a patient at the site 40 of an internal vein. Once the Central venous catheter is inserted, a small length of the Central venous catheter 31 remains external to the patient, extending outwards from the point of insertion 40. The external end of the Central venous catheter 31 is capped 32 to prevent bacteria, viruses or contaminants from entering the Central venous catheter 31. As shown in FIGS. 7 and 8, the small length of Central venous catheter 31 may be one tube 41 for a single internal lumen. As shown in FIGS. 9 and 10, the small length of Central venous catheter 31 may include two tubes 42 for a double internal lumen.

The end of the small length of the Central venous catheter 31 contains a cap 32. This cap 32 must be periodically replaced, typically weekly, to reduce the risk of contamination. Replacing the cap 32 must also be a sterile procedure that is conducted with washed hands, sterile gloves, sterile clothing, and alcohol swaps in a sterile environment.

The insertion point 40 of the Central venous catheter 31 may be covered with a traditional removable bandage 43. In this embodiment, this removable bandage 43 should only cover a very small portion of the external small length of the Central venous catheter 31 that is proximate to the insertion point 40.

In one embodiment of the subject invention, the chest wrap 25 may comprise a flexible substantially transparent or semi-transparent window (not shown) that traverses the external 30 and internal surfaces 29 of the looped 35 chest wrap 25. The chest wrap 25 should be aligned over the patient's chest 39 such that the flexible substantially transparent or semi-transparent window is over the Central venous catheter insertion point 40. In another embodiment of the subject invention, this substantially transparent window may be composed of a mesh or mesh-like material.

The chest wrap 25 is designed to cover and protect both the chest 39 and external short length of the Central venous catheter 31. The sleeve covers the Central venous catheter insertion area 40 and protects it from clothing, rubbing, and other external influences.

The chest wrap 25 comprises a first slit opening 44 proximate to the Central venous catheter insertion point 40. This slit opening 44 passes through the internal surface 29 to define an internal opening 45 that may be substantially parallel to the longitudinal axis of the looped 35 chest wrap 25. The slit opening 44 further passes into the internal lumen 47, beneath the external surface 30 to define an external opening 46 that may be substantially parallel to the longitudinal axis. The slit opening 44, the internal opening 45, the external opening 46, and the internal lumen 47 are all configured for receiving and removably holding the external small length of the Central venous catheter 31. In use, a patient moves the external small length of the Central venous catheter 31 and the distal end cap 32 through the slit opening 44 into the internal lumen 47 of the chest wrap 25.

Once the external small length of the Central venous catheter 31 is passed through slit opening 44, the Central venous catheter 31 is wrapped around the chest 39 of the patient through internal lumen 47.

The chest wrap 25 comprises a second slit opening 48. This slit opening 48 passes through the internal lumen 47 to define an internal opening 49 that may be substantially parallel to the longitudinal axis of the looped 35 chest wrap 25. The slit opening 48 further passes onto the external surface 30 to define an external opening 50 that may be substantially parallel to the longitudinal axis. The slit opening 48, the internal opening 49, and the external opening 50, are all configured for receiving and removably holding the external small length of the Central venous catheter 31. In use, a patient moves the external small length of the Central venous catheter 31 and the distal end cap 32 through the slit opening 48 onto the external surface 30 of the chest wrap 25.

The chest wrap 25 comprises a third slit opening 56. This slit opening 44 passes through the external surface 30 to define an internal opening 57 that may be substantially parallel to the longitudinal axis of the looped 35 chest wrap 25. The slit opening 56 further passes into a second lumen 59, beneath the external surface 30 to define an external opening 58 that may be substantially parallel to the longitudinal axis. The second lumen 59 is between the internal surface 29 and the external surface 30. The slit opening 56, the internal opening 57, the external opening 58, and the second internal lumen 59 are all configured for receiving and removably holding the external small length of the Central venous catheter 31. In use, a patient moves the external small length of the Central venous catheter 31 and the distal end cap 32 through the slit opening 56 into the internal lumen 47 of the chest wrap 25.

The chest wrap 25 further comprises a substantially flat strap 51 on the external surface 30. This strap 51 comprises a first end 52 and a second end 53 that are both attached to the external surface 30 of the chest wrap 25. The strap 51 may be substantially rectangular or square in shape. The central portion of the strap 54 is unattached to the chest wrap 25 to form a strap opening 55 that is configured for receiving and removably holding the external small length of the Central venous catheter 31 underneath the second lumen 59. This strap opening 55 may be substantially parallel to the longitudinal axis. In use, a patient moves the external small length of the Central venous catheter 31 and the distal end cap 32, already passed through the slit opening 48 into the second lumen 59, through the strap opening 55 underneath strap 51.

The strap 51 permits easy accessibility to the Central venous catheter 31 for medical professionals when administering infusion therapies without the need to remove the external small length of the Central venous catheter 31 from the slit opening 48 and the second lumen 59.

The slit opening 44, the slit opening 48, the slit opening 56, and the strap 51 are all substantially parallel with each other. The slit opening 44, the slit opening 48, the slit opening 56, and the strap 51 all comprise a fabric that applies sufficient compression force for holding the external small length of the Central venous catheter 31 and the distal end cap 32 on the patient's chest 39 such that this force does not substantially affect circulation, and keeps the external small length of the Central venous catheter 31 in place during treatment, sleep, and normal activities.

The slit opening 44, the slit opening 48, the slit opening 56, and the strap 51 prevent the external small length of the Central venous catheter 31 and the distal end cap 32 from contacting the patient's skin, eliminating the need for additional medical tape to secure the Central venous catheter 31 or the cap 32. This reduction of medical tape in the dressing reduces skin irritation for the patient.

In embodiments of the subject invention, the chest wrap 25, and the strap 51 may all be composed of a slightly flexible and lightweight fabric that stretches over a patient's chest 39 and is non-irritating to the skin. In embodiments of the subject invention, this fabric may be natural fibers, such as cottons, wools, silks, twills, cloths and bamboo; man-made fibers such as polyesters, nylons, tencels, viscose; or any combination of natural or man-made fibers and weaves.

What is claimed is:

1. A protective sleeve comprising: a stretchable tubular member having a proximal end with a first opening, a distal end with a second opening, a flat internal surface, a flat external surface, an elongated lumen extending between the first opening and second opening, wherein the elongated lumen is configured to slidably receive a patient's arm within the sleeve through the first opening through the elongated lumen and then through the second opening such that the elongated lumen is configured to contain a portion of the patient's arm within the sleeve such that the arm extends through both openings, wherein the sleeve is configured to be positioned on the arm without any gaps between the flat internal surface and the patient's skin, further wherein the sleeve is configured to be positioned on the arm over an intravenous needle skin insertion point; the sleeve further comprising a slit opening extending between the flat internal and flat external surfaces that is configured to be positioned proximate to the intravenous needle skin insertion point, further wherein the slit opening is configured to slidably receive a short length of tube extending from the intravenous needle skin insertion point through the slit opening; and the sleeve further comprising a substantially flat pocket disposed on the flat external surface, distal from the slit opening, wherein the substantially flat pocket comprises a pocket opening, wherein the pocket opening opens into the pocket above the flat external surface, further wherein the pocket opening is configured to receive the distal end of the short length of tube extending from the intravenous needle skin insertion point through the pocket opening into the pocket above the flat external surface; a flat strap located on the flat external surface, the flat strap comprising a first end and a second end and a central portion, wherein the first end and the second end are attached to the flat external surface and the central portion is unattached to the flat external surface to form an opening that is configured to receive a portion of the short length of tube extending from the intravenous needle skin insertion point, the flat strap located distal the slit opening and proximal the substantially flat pocket, wherein the slit opening, the flat strap and the pocket are configured to secure the short length of tube extending from the intravenous needle skin insertion point to the sleeve, wherein the tubular member comprises an unbroken whole cross-sectional circular shape from the first opening to the second opening.

2. The protective sleeve of claim 1, wherein the protective sleeve is configured to apply inward compression force over the flat internal surface of the sleeve to the patient's arm without inhibiting circulation.

3. The protective sleeve of claim 1, wherein the protective sleeve is configured to apply inward compression force such that the compression force maintains that sleeve on the patient's arm and secures the short length of tube extending from the intravenous needle without any additional fasteners.

4. The protective sleeve of claim 1, wherein the protective sleeve does not contain a fastener selected from the group consisting of hook and loop fasteners, buttons, clamps, brackets, buckles, magnets, snaps, tie straps, tape layers, or adhesives.

5. The protective sleeve of claim 1, wherein the protective sleeve is configured to be slid or rolled onto the patient's arm.

6. The protective sleeve of claim 1, wherein tubular member comprises a unitary tubular piece.

7. The protective sleeve of claim 1, wherein tubular member comprises an equal diameter from the first end to the second end.

8. The protective sleeve of claim 1, wherein tubular member comprises a cross-sectional shape of the sleeve selected from the group consisting of substantially circular and substantially elliptical.

9. The protective sleeve of claim 1, wherein the protective sleeve is wearable on either arm of a patient.

10. The protective sleeve of claim 1, wherein the protective sleeve further comprises a flexible substantially transparent window that traverses the flat external and flat internal surfaces of the sleeve.

11. The protective sleeve of claim 1, wherein the slit opening and the pocket disposed on the external surface are all substantially aligned with the longitudinal axis of the sleeve.

12. The protective sleeve of claim 1, wherein the sleeve comprises a fabric that is non-skin irritating.

13. The protective sleeve of claim 1, wherein the sleeve comprises a fabric that is selected from the group consisting of natural fibers, such as cottons, wools, silks, twills, cloths and bamboo; man-made fibers such as polyesters, nylons, tencels, viscose; and any combination of natural or man-made fibers and weaves.

* * * * *